(12) United States Patent
Singh et al.

(10) Patent No.: US 9,266,818 B2
(45) Date of Patent: Feb. 23, 2016

(54) PROCESS FOR PURIFICATION OF FREE BIO-AMINO ACIDS

(71) Applicants: Harsh Pratap Singh, Himachal Pradesh (IN); Ajay Rana, Himachal Pradesh (IN)

(72) Inventors: Harsh Pratap Singh, Himachal Pradesh (IN); Ajay Rana, Himachal Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/376,631

(22) PCT Filed: Feb. 8, 2013

(86) PCT No.: PCT/IN2013/000088
§ 371 (c)(1),
(2) Date: Aug. 5, 2014

(87) PCT Pub. No.: WO2013/118152
PCT Pub. Date: Aug. 15, 2013

(65) Prior Publication Data
US 2015/0051422 A1 Feb. 19, 2015

(30) Foreign Application Priority Data

Feb. 10, 2012 (IN) .......................... 0371/DEL/2012

(51) Int. Cl.
*C07C 227/40* (2006.01)
*C07C 237/06* (2006.01)

(52) U.S. Cl.
CPC .................................. *C07C 227/40* (2013.01)

(58) Field of Classification Search
CPC ............................ C07C 227/40; C07C 237/06
USPC ........................................................ 562/554
See application file for complete search history.

(56) References Cited

U.S. PATENT DOCUMENTS

| 5,017,480 A | 5/1991 | Mori et al. |
| 2005/0084544 A1 | 4/2005 | Ekanayake et al. |
| 2006/0105437 A1 | 5/2006 | Tachiki et al. |
| 2008/0300421 A1 | 12/2008 | Baudouin |

FOREIGN PATENT DOCUMENTS

IN    2601/DEL/2008    *    1/2011

OTHER PUBLICATIONS

Cartier ("The Utility of Polymeric Reversed Phase Packings for the Purification of Peptides, Proteins, and Antibiotics", 1990, p. 275-284 of "Separation for Biotechnology 2", ISBN-13: 978-94-010-6839-0, e-ISBN 13: 978-94-009-0783-6).*
Resindion technical data sheet for Sepabeads EC-EP, obtained online on Jul. 1, 2015, 1 page.*
Rohm and Haas technical data sheet for Amberchrom CG161, obtained online Jul. 1, 2015, p. 1-5.*
International Search Report dated Jul. 12, 2013 for PCT application No. PCT/IN2013/000088.

* cited by examiner

*Primary Examiner* — Jafar Parsa
*Assistant Examiner* — Amy C Bonaparte
(74) *Attorney, Agent, or Firm* — Ohlandt, Greeley, Ruggiero & Perle, L.L.P.

(57) ABSTRACT

The present invention relates to a green process for purification of free bio amino acids from plant parts, particularly tea leaves and shoots. The invention more particularly relates to an organic solvent free, fast and economical process for purification of natural amino acids on large scale without using any chemical, acid or alkali substance. The invention also relates to a process for purification of bio amino acids from plant and plant parts (renewable bioresources) which are rich in free amino acids.

4 Claims, 8 Drawing Sheets

A Schematic Flow Chart Showing Process for Amino Acids Purification

Figure 1- A Schematic Flow Chart Showing Process for Amino Acids Purification
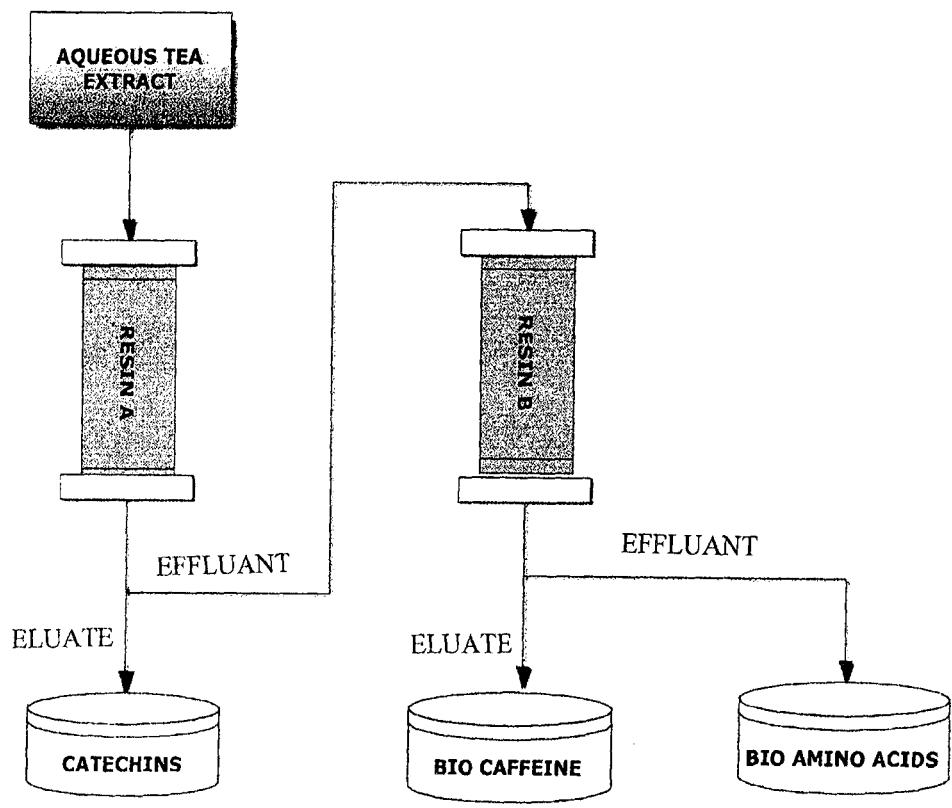

Figure 2a. RP- HPLC Chromatogram of tea bio amino acids (theanine enriched)
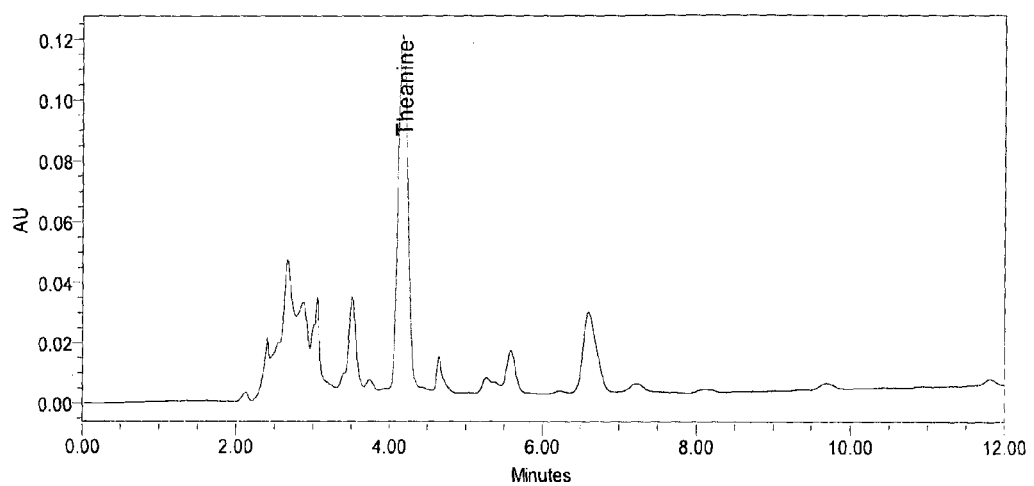

Figure 2b. RP-HPLC Chromatogram of standard theanine
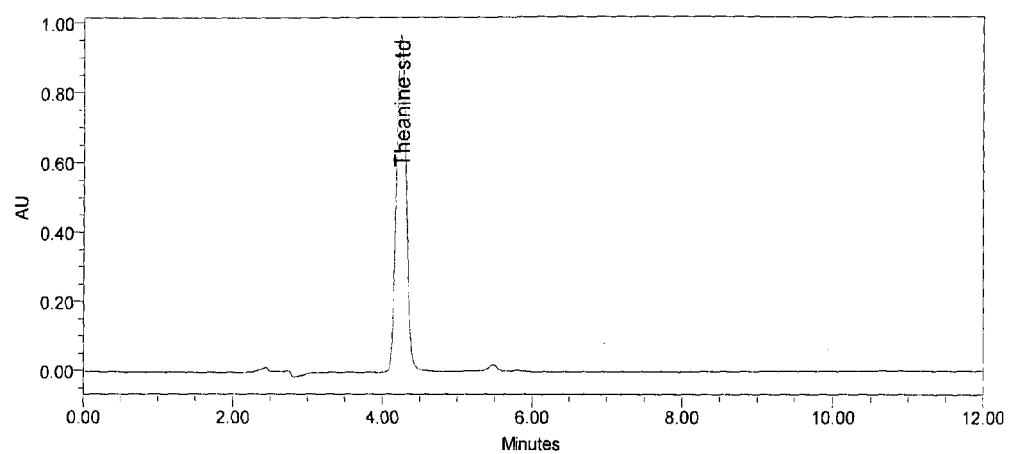

Figure 3a. UPLC chromatogram of standard amino acids
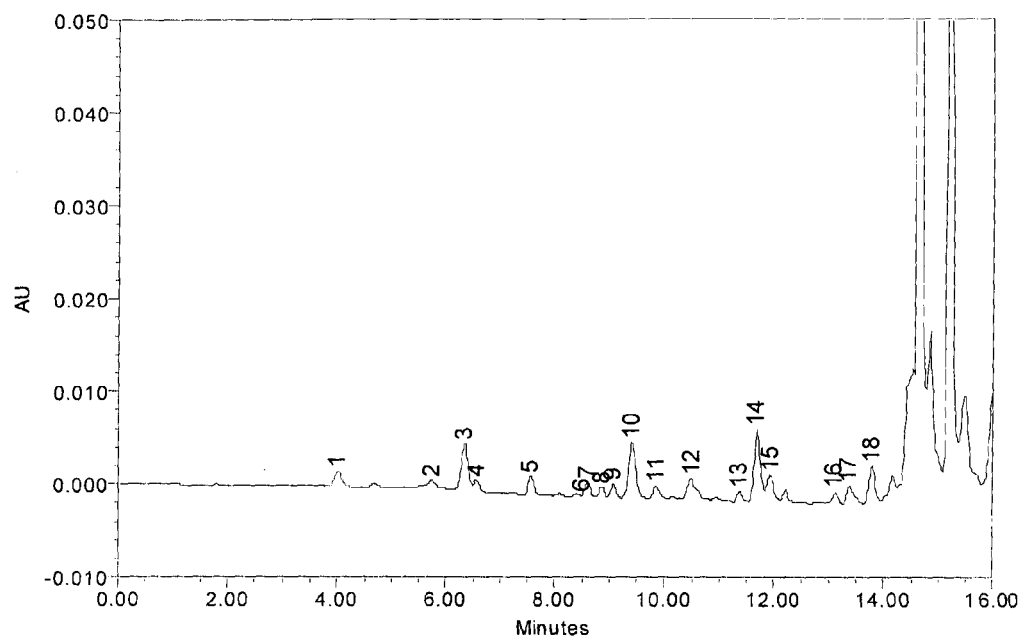

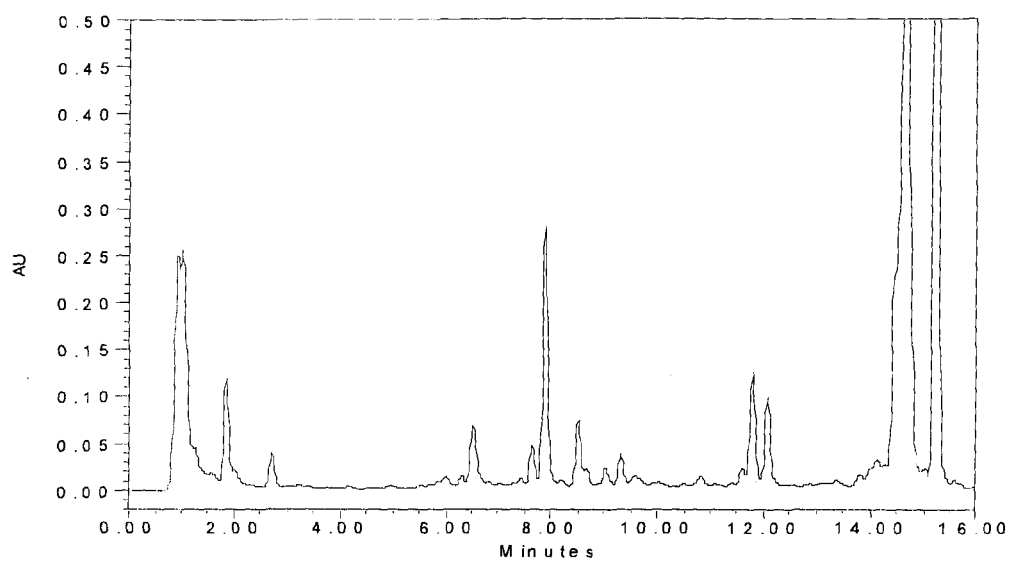
Figure 3b. UPLC chromatogram of tea bio amino acids

Figure 3c. UPLC Chromatogram of Sesbania bio amino acids
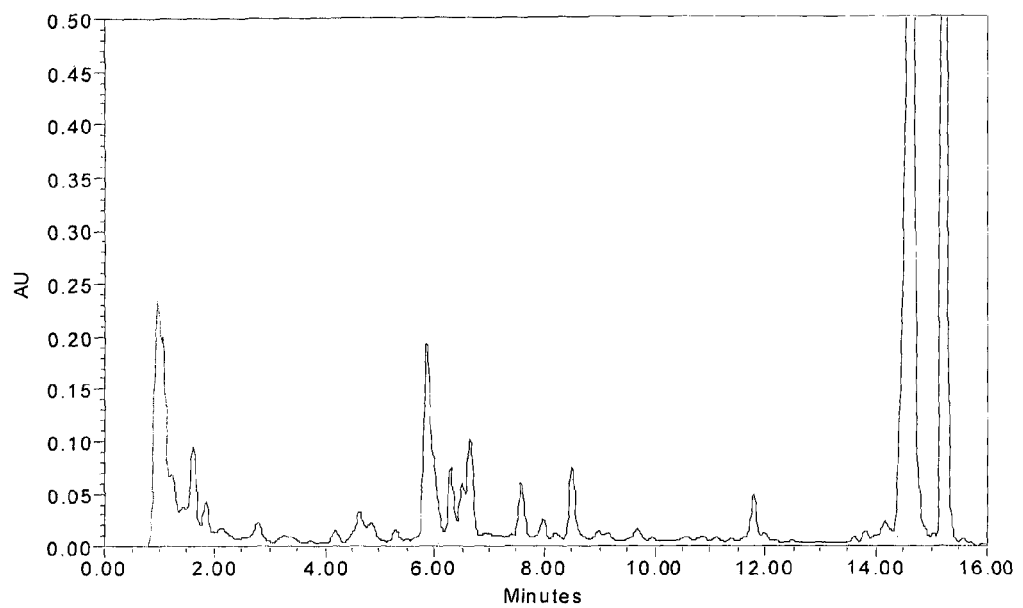

Figure 4a. RP-HPLC chromatogram of tea bio amino acids
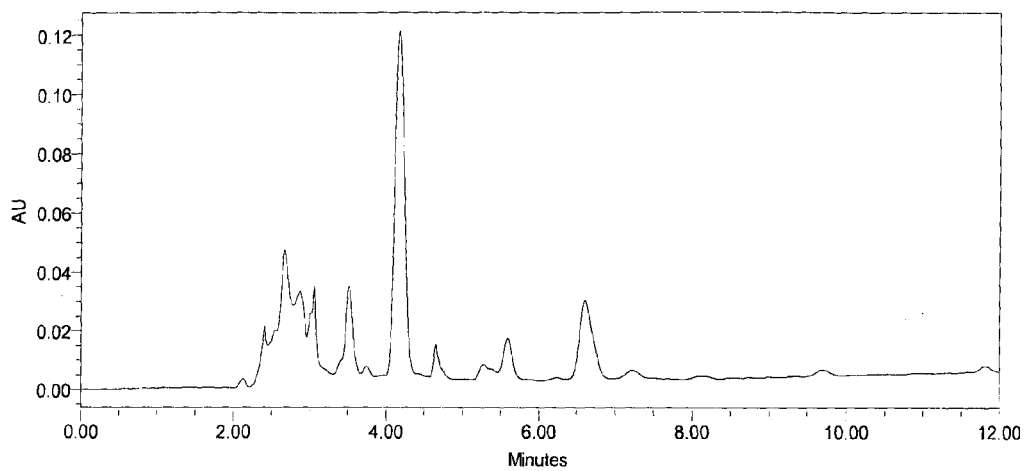

Figure 4b. RP-HPLC chromatogram of Sesbania bio amino acids
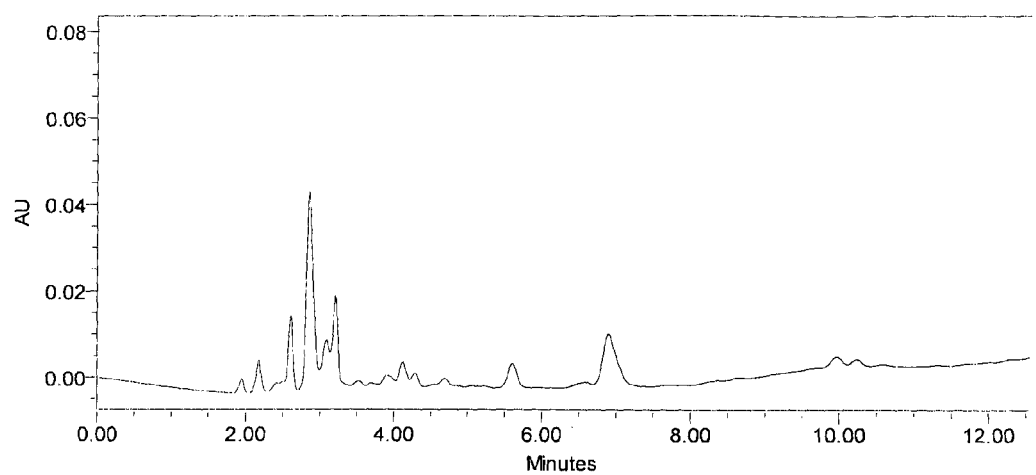

PROCESS FOR PURIFICATION OF FREE BIO-AMINO ACIDS

The following specification particularly describes the invention and the manner in which it is to be performed.

FIELD OF INVENTION

The present invention relates to an improved process for purification of free bio amino acids (theanine enriched) from parts of plants, preferably from tea (*Camellia sinensis*). Particularly, the invention relates to an economical process for purification of natural free amino acids from plant and plant parts like leaves, flowers and fruits (renewable bioresources) without using any chemical substance, acid or alkali. More particularly the invention relates to a low cost, green process for purification of fraction containing natural free amino acids; to be used as readily bioavailable nutritional supplements, especially for vegetarians and protein deficient people as an option for costlier protein supplements.

BACKGROUND OF THE INVENTION

The amino acids are the building blocks of proteins and act as intermediates in body metabolism. The importance of amino acids as building blocks of proteins for the growth and repair of muscles, bones, skin, tendons, ligaments, hair, eyes and other tissues is proven since a very long time. Proteins play a vital role in various body functions such as, metabolism, cell signalling, the immune system, cell adhesion and cell cycle. The problem of protein deficiency is very common among populations of poor, undeveloped and in developing countries. Even in developed nations, this problem of protein deficiency was reported in certain groups of population with specific diet habits. Particularly, vegetarians need to be very careful about eating the right combinations of plant foods to get enough of the essential amino acids. When proteins enter the body; first they are broken down into amino acids during the digestion process. The amino acids are then used in different areas of the body where they are needed for protein synthesis. The amino acids are also responsible for the biological activities of proteins. So, the amino acids which are the building blocks of proteins are vital for body functioning. So there exist huge potential of using amino acids in form of nutritional supplements.

Generally there are 20 standard amino acids which constitute the proteins, and out of these only 10 are synthesized in our body. The other 10 which are not synthesized in our body are called as essential amino acids viz. alanine, asparagine, aspartic acid, cysteine, glutamic acid, glutamine, glycine, proline, serine and tyrosine. We need to obtain these essential amino acids from our diet and failure to obtain any of essential amino acid, could results in degradation of the body's proteins and other associated problems.

As plant and plant parts like leaves, flowers, fruits, seeds and vegetables are considered as rich source of free amino acids. Therefore these plant and plant parts could be used as natural and renewable sources to obtain these essential components. Also, in recent decades there has been found an immense interest in nutraceuticals, dietary health supplements and extracts which were obtained from natural sources in comparison to those with synthetic origin.

Tea (*Camellia sinensis*) of Theaceae family is known world wide as a beverage crop. This plant is also a good source of free amino acids. The amino acids content in the tea was estimated from 3-4% on dry wt. basis. The presence of free amino acids in tea is well known and it was reported that it contains all the 20 amino acids. The presence of different amino acids in tea like; alanine, arginine, asparagine, aspartic acid, glutamic acid, isoleucine, histidine, leucine, phenylalanine, serine, theanine, threonine, and tyrosine have been determined by amino acid analyzer as well as by HPLC analysis (Wang et al., Analysis of free amino acids in Chinese teas and flower of tea plant by high performance liquid chromatography combined with solid-phase extraction. Food Chemistry, 123, 2010, 1259-1266; Jean-Philippe Veyssier, Analysis of Theanine in Green Tea using the Biochrom 30 Amino Acid Analyser. Biochrom Ltd. Cambridge, UK; Ulrich H. Engelhardt, Chemistry of Tea, 2010 Elsevier Ltd.). Tea contains all the essential amino acids along with non-essential ones. Along with that, tea also contains a unique non-protein derived amino acid called as theanine which was formed from glutamine and ethylamine (Vuong et al., Journal of Science of Food and Agriculture, 2011, 91, 1931-1939).

Theanine is well known as a psychoactive amino acid which crosses the blood brain barrier and relaxes during stress. High water solubility of theanine in comparison to caffeine and catechins and its presence in sufficient amount in tea plant is an important requisite of the present invention; as it constitutes up to 50% of total amino acids present in the tea.

Though, Ekanayake et al. (U.S. patent application Ser. No. 10/689,910) has explained a process for isolation of theanine by extraction, absorption and filtration from plant material using isopropanol as a solvent to get theanine enriched extract. They used polyamides, polyvinylpyrollidine and polycar as adsorbants.

While, Tachiki et al. (U.S. patent application Ser. No. 10/523,098) has developed a synthetic method using glutaminase derived from the bacteria in a mixture of glutamine and ethylamine at alkaline pH (9-12).

Even there are few studies in literature which report sublimation process to obtain amino acids from natural samples (Daniel and Jeffrey, Analytical Chemistry 1998, 70, 3119-3122), but amino acid decomposition in to amines as well as deamination of amino acids at high temperature are the major problems in sublimation process.

Also according to Basiuk et al., there are more chances of formation of dipeptides and diketopiperazines in vapor phase of sublimation process. Also Fisher et al. (U.S. patent application Ser. No. 10/111,919) disclosed a process of purification of amino acids by electrodialysis followed by fermentation process to get amino acids.

Tea contains all the essential amino acids like, threonine, valine, leucine, isoleucine, lysine, phenylalanine and trytophan in it. So the present invention was specially focused on obtaining all these free amino acids present in tea along with theanine by an economical and green process methodology.

With ever increasing interest in naturally obtained food supplements, nutraceutiacls and additives: their market is also growing at very fast rate world wide. This might be due to health safety and therapeutic potential associated with them. So, in an attempt to obtain natural bio amino acids by a low cost green methodology and as an option for costlier protein supplements; the present invention was carried out.

As the free amino acids are readily available in the body and elevates its level in the general circulation within 15 minutes (Barry Finnin and Samuel Peters, Amino acids and Bodybuilding, Muscle and Fitness Magazine, April 1996) if consumed as supplements in comparison to protein supplements. Also, proteins first undergo enzymatic degradation in the alimentary canal for their catabolism into constituent free amino acids. So, in this invention we have disclosed an economical and green process for purification of free bio amino acids (theanine enriched) from tea shoots and from other plants and plant parts (renewable bioresources like leaves, fruits and flowers) which are good source of free amino acids.

There exist very few process methodologies which show extraction and purification of free amino acids from plant sources by green and economical process. While most of the earlier reported/developed processes and methodologies for purification of amino acids (ion exchange, sublimation, adsorption, electrodialysis etc.) generally involve usage of chemical substances, organic solvents, acids and alkali, leading to many disadvantages such as amino acid decomposition into amines as well as deamination of amino acids, the present invention totally excludes the use of all these chemical substances during the whole process of obtaining these natural bio amino acids.

OBJECTIVE OF THE INVENTION

The main objective of the present invention is to develop a green and economical aqueous process for purification of free bio amino acids from plant sources/renewable bioresources.

Another objective of the present invention is to purify free amino acids of tea along with theanine.

Still another objective of the present invention is to purify bio amino acids; so as to make them completely free from other major constituents of plants like tannins, lipids, alkaloids, catechins & caffeine in case of tea.

Yet another objective of the invention is to purify bio amino acids in their natural form by avoiding use of any type of chemical substance like organic solvents, acids and alkali.

BRIEF DESCRIPTION OF FIGURES AND DRAWINGS

The accompanying drawings illustrate embodiments of the invention and, together with the description, serve to explain the invention. These drawings are offered by way of illustration and not by way of limitation.

FIG. 1 illustrates a schematic flow chart of process for purification of bio amino acids.

FIG. 2a; RP-HPLC Chromatogram of tea bio amino acids (theanine enriched) and FIG. 2b; HPLC Chromatogram of standard theanine FIG. 3a; UPLC Chromatogram of mixture of amino acids standards, FIG. 3b; UPLC Chromatogram of tea bio amino acids (theanine enriched) and FIG. 3c; UPLC Chromatogram of *Sesbania grandiflora* bio amino acids.

FIG. 4a; RP-HPLC chromatogram of tea bio amino acids and FIG. 4b; RP-HPLC chromatogram of *Sesbania* bio amino acids.

SUMMARY OF THE INVENTION

The present invention relates to an improved process for purification of free bio amino acids from natural sources like plants and plant parts by a solvent free and economical process.

Accordingly the present invention provides an improved process for production of free bio amino acids said process comprising:
 a. extracting parts of plants rich in amino acids with water,
 b. filtering the aqueous plant extract obtained in step (a) through cotton filters and obtaining filtered aqueous extract,
 c. passing the filtered aqueous extract of step (b) through a first column packed with polymethacrylate based resin with particle size of 100-300 microns and saturated with water preferably with double distilled water, to get polyphenol free effluent,
 d. passing the polyphenol free effluent of step (c) through a second column packed with polystyrene divinylbenzene polymer based resin with particle size of 120 microns, saturated with double distilled water and obtaining the effluent,
 e. concentrating the effluent of step (d) containing free bio amino acids.

DETAILED DESCRIPTION OF THE INVENTION

The present invention is described with reference to the tables/figures etc. and specific embodiments; this description is not meant to be construed in a limiting sense. Various alternate embodiments of the invention will become apparent to persons skilled in the art, upon reference to the description of the invention. It is therefore contemplated that such alternative embodiments form part of the present invention.

Unless defined otherwise, technical and scientific terms used herein have the same meaning as commonly understood by one of ordinary skill in the art to which this invention belongs. Some of the terms are defined briefly herebelow; the definitions should not be construed in a limiting sense.

The term "bio amino acids" used herein relates to the purely natural free amino acids fraction (theanine rich) from the tea shoots in particular and from other plant renewable parts like fruits, leaves, flowers, and seeds. These bio amino acids are pure and 100% natural fraction, obtained especially from natural sources like plants and plant parts without using any extraneous chemical substance or acid and alkali.

The term "tea shoots" is used herein for fresh tea leaves along with stem portion. The term "completely free from polyphenols" means that purified bio amino acids fraction contains no caffeine, lipids, saponins, alkaloids and catechins as detected by RP-HPLC analysis.

The term "renewable resources" is used herein for leaves, fruits, flowers and seeds of plants and more preferably for leaves.

The term "effluent" is used herein for the material which doesn't get adsorbed in the resin columns (A and B), and was eluted along with water which is the mobile phase.

The term "elluate" is used herein for the resin bound material/compounds.

The term "water" as used herein refers to distill water, deionized water and more preferably double distilled water.

Both the resin column (A) polymethacrylate based and (B) polystyrene divinylbenzene polymer based resin were used in the present invention for bio amino acids purification were packed in water, most preferably in double distilled water.

Process of the Invention:

1. The first step of the present invention relates to the aqueous extraction of the fresh tea shoots, which is done by any of the following methods:
 a. Freeze drying the plant parts at −20° C., crushing the freezed plant parts to powder form, extracting the freezed and crushed plant parts with warm water (60° C.).
 b. Drying the fresh plant parts, grinding the dried plant parts to powder form, extracting the ground powdered leaves with cold water (25° C.).
 c. Directly extracting the fresh plant parts with hot water (90° C.).

Thus for extraction these three methodologies are used in the present invention. 100 gm of fresh shoots are taken in each case and extracted individually with 600 ml of water for 15-30 min.

2. The aqueous extract obtained from different extraction steps is then filtered twice using cotton (adsorbent) filter.

3. Purification by Adsorption Column Chromatography:

The purification of free amino acids from the filtered aqueous extract is done by using adsorption column chromatography using two different adsorption resins both of which differs in their chemistry and particle size. The adsorption is a surface phenomenon which involves weak and reversible binding of selective compounds or molecules present in the mixture with the surface of stationary phase. So, herein the present invention the free amino acids are purified by selecting two different resins in series and by removing other major components present in the extracts. The resin (A) used herein in the present invention is a polymethacrylate based resin preferably SEPABEADS™ resin with particle size of 100-300 microns, while resin (B) used herein in the present invention is a polystyrene divinylbenzene polymer based resin preferably AMBERCHROM™ resin with particle size of 120 microns.

The filtered aqueous extracts were then passed through prepacked resin column (A) polymethacrylate based resin with particle size of 100-300 microns. The column was packed and saturated in water more preferably with double distilled water. This resin column adsorbs the polyphenols and other complex molecules allowing only amino acids, proteins and caffeine to pass through along with water as effluent.

Now the aqueous effluent of resin column A containing proteins, caffeine and amino acids are then passed through another column packed with polystyrene divinylbenzene polymer based resin (B) with particle size of 120 microns. This resin column is also packed and saturated with water preferably with double distilled water in a glass column. This polymeric resin column with very fine particle size allows only bio amino acids to pass through along with water by adsorbing caffeine and proteins completely.

Bio Amino Acids Fraction:

The effluent aqueous fraction contains natural bio amino acids and is completely free from catechins and caffeine which are other major constituents of tea. This aqueous fraction containing free bio amino acids theanine enriched in case of tea (FIG. 2a) compared with standard theanine (FIG. 2b), is then concentrated with rotary evaporator followed by spray drying or through lyophilization by freeze drying to obtain off white to light brown colored powder. The bio amino acids fraction is further analyzed by paper chromatography and RP-HPLC (FIG. 4a, 4b) and UPLC (FIG. 3b, 3c) analysis. The results of RP-HPLC significantly shows the presence of theanine as major component among the tea bio amino acids as major constituents. This is confirmed by running standard theanine by the same method and under similar condition in which tea bio amino acid fraction is analyzed and also by comparison of peak retention time and absorbance as well. These results clearly show that the bio amino acids fraction is enriched with theanine, as major constituent. Further the UPLC analysis also shows the significance of the fraction containing the other amino acids when their retention was compared with that of mixture of the standard amino acids.

Accordingly, the invention provides a process for purification of free bio amino acids form natural sources like plants and plant parts, especially from those which are rich source of free amino acids. The present invention discloses a process developed by using combination of adsorption resins of different particle size and chemistry to purify bio amino acids (theanine enriched) (FIG. 2a) fraction from tea shoots and completely free from polyphenols catechins, lipids, saponins, alkaloids and caffeine.

In yet another embodiment, the solvent free process for purification of free bio amino acids comprises the following steps:
 a. extracting parts of plants rich in amino acids with water,
 b. filtering the aqueous plant extract obtained in step (a) through cotton filters and obtaining filtered aqueous extract,
 c. passing the filtered aqueous extract of step (b) through a first column packed with polymethacrylate based resin with particle size of 100-300 microns and saturated with water preferably with double distilled water, to get polyphenol free effluent,
 d. passing the polyphenol free effluent of step (c) through a second column packed with polystyrene divinylbenzene polymer based resin with particle size of 120 microns, saturated with double distilled water and obtaining the effluent,
 e. concentrating the effluent of step (d) containing free bio amino.

In yet another embodiment, the plant parts used is theanine rich leaves or shoots such as tea leaves or shoots or any other plant part which contains free amino acids.

In still another embodiment the extraction is done by any of the following methods:
 a. Freeze drying the plant parts at $-20°$ C., crushing the freezed plant parts to powder form and extracting the freezed and crushed plant parts with warm water ($60°$ C.).
 b. Drying the fresh plant parts, grinding the dried plant parts to powder form and extracting the ground powdered leaves with cold water ($25°$ C.).
 c. Directly extracting the fresh plant parts with hot water ($90°$ C.).

In yet another embodiment the polymethacrylate based resin is preferably SEPABEADS™ resin.

In yet another embodiment the polystyrene divinylbenzene polymer based resin is preferably AMBERCHROM™ resin.

In yet another embodiment the concentration is done with rotary evaporator followed by spray drying, optionally through lyophillization by freeze drying.

In yet another embodiment the bio amino acids obtained are completely free from tea polyphenols (catechins), caffeine and other major constituents of tea leaves.

In yet another embodiment of the present invention a process has been described for utilization of plants renewable bioresources like fruits, leaves, flowers, and seeds especially leaves as rich source of readily bioavailable free bio amino acids.

In yet another embodiment, the present invention described a green process without using chemical substances, acids and alkali to purify free bio amino acids as readily bioavailable source, compared to costly protein supplements.

EXAMPLES

Example 1

About 100 gm of fresh tea shoots were taken. The shoots were then placed in a deep freezer at $-20°$ C. The freezed shoots were crushed after some time 6-8 hrs followed by extraction with hot water ($60°$ C.) for 15-20 min. The extract was filtered twice with cotton filter. Then the extract was passed through resin column (A) of polymethacrylate based resin, which was packed in double distilled water. The water was used as effluent which takes amino acids and caffeine along with it, leaving behind polyphenolic components adsorbed in the column. This aqueous fraction containing caffeine and amino acids was then passed though another resin column (B) of polystyrene divinylbenzene polymer resin again packed in double distilled water. This column adsorbs the caffeine, proteins and other impurities allowing bio amino acids to pass through the column along with water. Thus this aqueous fraction contains purified bio amino acids. Dry the aqueous fraction to get pure bio amino acids by spray drying. The RP-HPLC chromatogram shows the presence of amino acids (theanine enriched) (FIG. 2a) compared with the standard theanine (FIG. 2b).

Example 2

About 1 kg of tea shoots was taken. The tea shoots were placed in a deep freezer at −20° C. Freezed shoots were crushed and then extracted with hot water (60° C.) for 20 min. The extract was filtered twice with cotton filter. Finally the aqueous extract was passed through resin column (A) of polymethacrylate based resin and packed in double distilled water. The water was used as effluent which takes along with it, amino acids and caffeine from the column leaving behind polyphenolic components (catechins) adsorbed in the column. This aqueous fraction containing caffeine and amino acids was then again passed though another resin column (B) of polystyrene divinylbenzene polymer resin packed and saturated with double distilled water. This column absorbs the caffeine and other impurities allowing only free bio amino acids to pass through the column along with solvent (water). Thus the obtained aqueous fraction contains purified bio amino acids. This fraction was dried to evaporate the water from it by spray drying to get powder form. The UPLC chromatogram shows the presence of amino acids (FIG. 3b) compared with the chromatogram of standard amino acids (FIG. 3a).

Example 3

About 500 gm of *Sesbania grandiflora* leaves were collected and then placed in a deep freezer at −20° C. The freezed leaves were then extracted with hot water (60° C.) for 20 min. The extract was filtered twice with cotton filter. Finally the aqueous extract was passed through resin column (A) of polymethacrylate based resin and was packed in double distilled water. The water was used as effluent which takes along with it, amino acids and other low molecular weight phenolics from the column leaving behind high molecular weight polyphenolic and other impurities adsorbed in the column. This effluent of column A was then again passed though another resin column (B) of polystyrene divinylbenzene polymer resin. This column absorbs the low molecular weight phenolics and other impurities allowing only bio amino acids to pass through the column along with water. Thus the obtained aqueous fraction which contains purified natural bio amino acids. This fraction was then spray dried to get offwhite colored powder. The UPLC chromatogram shows the presence of amino acids (FIG. 3c) compared with the chromatogram of standard amino acids (FIG. 3a) and RP-HPLC chromatogram of bio amino acids (FIG. 4b).

Advantages

The following are the main advantages of present invention:
1. Develops a new economical process for purification of free natural bio amino acids from tea shoots.
2. Purification of theanine enriched free bio amino acids from tea shoots.
3. The bio amino acids are completely free from tea polyphenols (catechins) and caffeine which are other major constituents of tea.
4. An economical green process to obtain free bio amino acids on large scale from plants and their parts (renewable bioresources) especially from those which are rich source of free amino acids.
5. Purified natural free amino acids can be used as a source of more readily bioavailable health supplements as compared to costly protein supplements.
6. Low cost natural free amino acid supplements could be very much beneficial for vegetarians and protein deficient peoples.

The invention claimed is:
1. A process for purification of free bio amino acids, said process comprising:
   a. extracting plant parts rich in free amino acids with deionized water or double distilled water to obtain an aqueous extract,
   b. filtering the aqueous extract obtained in step (a) through cotton filters to obtain a filtered aqueous extract,
   c. passing the filtered aqueous extract of step (b) through a first column packed with polymethacrylate based resin with particle size of 100-300 microns and saturated with water to obtain a polyphenol free effluent,
   d. passing the obtained polyphenol free effluent of step (c) through a second column packed with a polystyrene divinylbenzene polymer based resin with particle size of 120 microns saturated with deionized water or double distilled water to form a second effluent,
   e. concentrating the second effluent of step (d) containing free bio amino acids with a rotary evaporator followed by spray drying or through lyophilization by freeze drying to a obtain a white to light brown colored free amino acid rich powder.
2. The process as claimed in claim 1, wherein the plant parts used in step (a) are theanine enriched leaves and shoots of *Camellia sinensis* tea or any other plant parts that contain free amino acids.
3. The process as claimed in claim 1, wherein the extraction is done by any of the following methods:
   a. freeze drying the plant parts at −20° C. to form frozen plant parts, crushing the frozen plant parts to powder form to form frozen crushed plant parts and extracting the frozen crushed plant parts with warm water at 60° C.
   b. drying the plant parts to form dried plant parts, grinding the dried plant parts to powder form to form ground powdered plant parts and extracting the ground powdered plant parts with cold water at 25° C.
   c. directly extracting the fresh plant parts with hot water at 90° C.
4. The process as claimed in claim 1, wherein the bio amino acids obtained are completely free from polyphenols, catechins, caffeine, and other major constituents of tea leaves.

* * * * *